(12) United States Patent
Walker

(10) Patent No.: US 6,682,606 B2
(45) Date of Patent: Jan. 27, 2004

(54) SYSTEM AND METHOD OF TREATING A POROUS MATERIAL OF A VEHICLE

(75) Inventor: Thomas R. Walker, Farmington Hills, MI (US)

(73) Assignee: Ziebart International Corporation, Troy, MI (US)

( * ) Notice: Subject to any disclaimer, the term of this patent is extended or adjusted under 35 U.S.C. 154(b) by 328 days.

(21) Appl. No.: 09/834,091

(22) Filed: Apr. 12, 2001

(65) Prior Publication Data

US 2003/0053929 A1 Mar. 20, 2003

(51) Int. Cl.⁷ .............................. A61L 2/18; B08B 3/04; B08B 3/08; B08B 5/04

(52) U.S. Cl. ............................... 134/6; 134/21; 134/26; 422/5; 422/28; 422/37

(58) Field of Search ............................... 134/6, 26, 21; 422/5, 28, 37

(56) References Cited

U.S. PATENT DOCUMENTS 3,891,149 A * 6/1975 Rendemonti ................. 239/70
4,137,952 A * 2/1979 Rendemonti ................. 141/27

* cited by examiner

Primary Examiner—Zeinab El-Arini
(74) Attorney, Agent, or Firm—Brooks Kushman, P.C.

(57) ABSTRACT

The present invention involves a system and method of treating a porous material of a vehicle wherein the porous material has microorganisms. The method includes providing first and second antimicrobial solutions. The method further includes applying the first antimicrobial solution to the porous material and scrubbing the first antimicrobial solution and the porous material so that the first solution contacts the microorganisms. The method further includes applying the second antimicrobial solution heated at a predetermined temperature to the porous material after a predetermined time upon applying the first solution. The method further includes removing the first and second antimicrobial solutions and the microorganisms from the porous material.

16 Claims, 3 Drawing Sheets

SYSTEM AND METHOD OF TREATING A POROUS MATERIAL OF A VEHICLE

BACKGROUND OF THE INVENTION

1. Field of the Invention

The present invention relates to a system and method of treating a porous material of a vehicle, wherein the porous material has microorganisms therein.

2. Background Art

The industry of vehicle cleaning and detailing has been established for a substantial period. Many entities provide services which include exterior and interior cleaning of vehicles. As known, typical services to clean and detail an interior of a vehicle may include vacuuming floor carpets, buffing interior panels, shining windows, to name a few. Such services certainly provide adequate means in cleaning the interior of a vehicle.

There is a growing concern of the spread and infection of undesirable microorganisms, even in vehicles. Active lifestyles and current vehicle usage may introduce and facilitate germ growth via food, beverages, pets, body fluids, etc. Thus, there is also an increasing need for cost effective cleaning and eliminating undesirable microorganisms such as bacteria and viruses from vehicles. Whether a situation involves a change of ownership of a vehicle or simply routine cleaning desired by the current owner of a vehicle, undesirable microorganisms will typically exist in the interior of the vehicle. With the growing technology of measuring bacterial content on an area, standards of cleanliness have risen and tolerance thresholds have been lowered.

SUMMARY OF THE INVENTION

Thus, it is an object of the present invention to provide a simple and cost effective way of treating an interior of a vehicle having undesirable microorganisms.

It is an object of the present invention to provide a method of treating a porous material of a vehicle, wherein the porous material has microorganisms. The method includes providing first and second antimicrobial solutions and applying the first antimicrobial solution to the porous material. The method further includes scrubbing the first antimicrobial solution and the porous material so that the first solution contacts the microorganisms, and applying the second antimicrobial solution heated at a predetermined temperature to the porous material after a predetermined time upon applying the first solution. The method further includes removing the first and second antimicrobial solutions and the microorganisms from the porous material.

Another embodiment of the present invention provides a method of removing bacteria from a fabric of a vehicle compartment, wherein the fabric has bacteria. The method includes providing first and second antimicrobial solutions and applying the first antimicrobial solution to the fabric. The method further includes scrubbing the first antimicrobial solution and the fabric so that the first solution contacts the bacteria to begin disinfection of the fabric and to loosen the bacteria on the fabric. The method further includes applying the second antimicrobial solution on the fabric to further disinfect and deodorize the fabric after a predetermined time period upon applying the first solution. The method further includes immediately removing the first and second solutions and the bacteria from the fabric as the second microbial solution is applied.

Another embodiment of the present invention provides a method of treating a vehicle wherein the vehicle has interior and exterior portions and glass. The interior portion includes a trim, a fabric, instruments, and a vent duct having bacteria. The method includes providing first, second, and third antimicrobial solutions. The method further includes washing the exterior portion of the vehicle and vacuuming the interior portion of the vehicle to remove loose dirt therefrom. The method further includes applying the first antimicrobial solution to the fabric, and scrubbing the first antimicrobial solution and the fabric so that the first solution contacts the bacteria to begin disinfection of the fabric. Next, the method comprises applying the second antimicrobial solution on the fabric to further disinfect and deodorize the fabric after a predetermined time upon applying the first solution, and immediately removing the first and second solutions and the bacteria from the fabric as the second solution is applied, and then reapplying the second solution to the fabric. Moreover, the method comprises applying the first solution to the trim for disinfection thereof and rinsing the first solution from the trim. Additionally, the method includes applying the second solution onto the instruments and vent ducts for disinfection thereof and applying the third solution onto the glass for disinfection thereof. Furthermore, the method includes inspecting the interior and exterior portion for completeness.

DETAILED DESCRIPTION OF THE PREFERRED EMBODIMENTS

Figure 1:
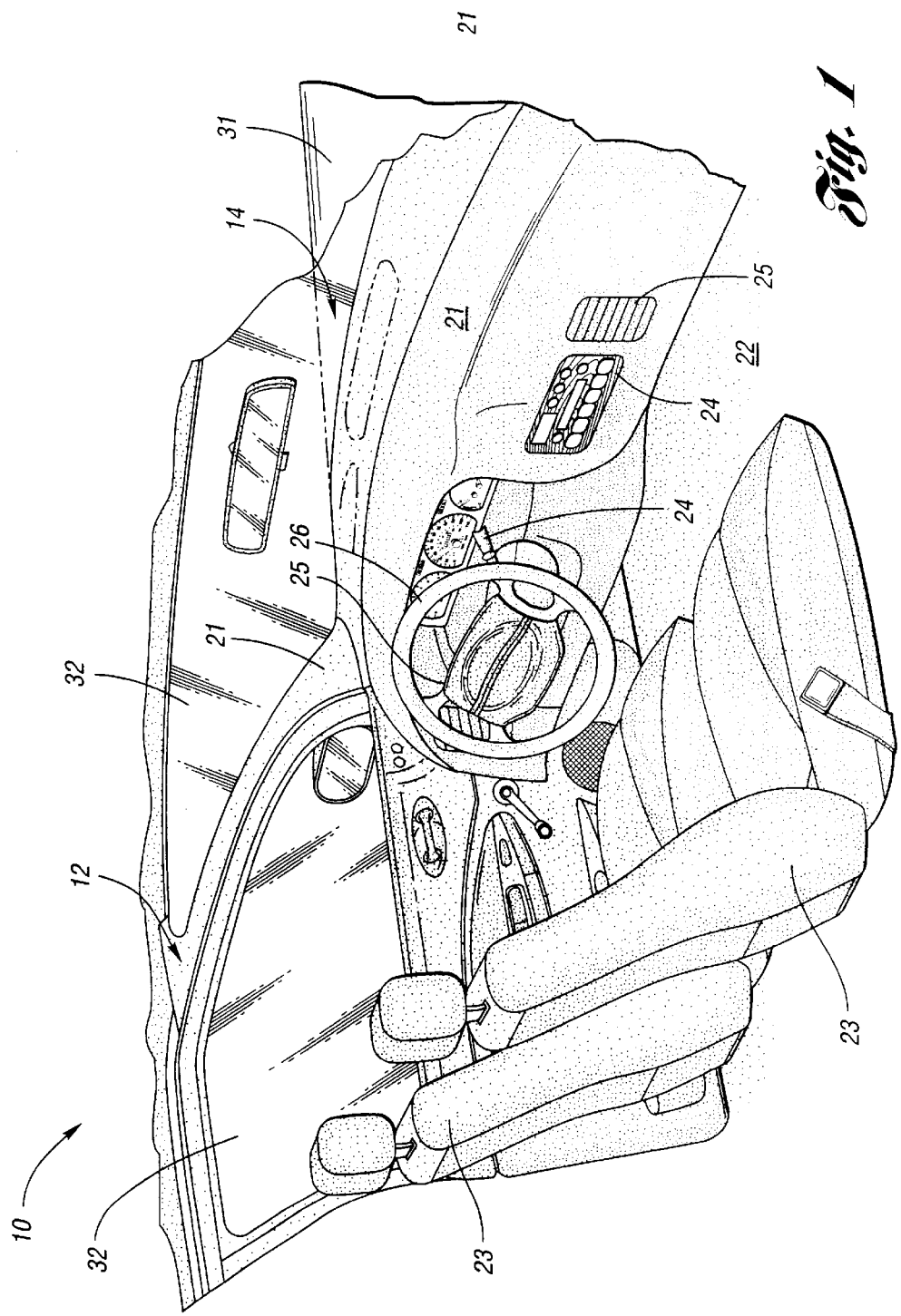
FIG. 1 is a perspective view in-part of an interior portion and an exterior portion of a vehicle in accordance with the present invention.

FIG. 1 illustrates a vehicle 10 in-part having interior and exterior portions 12, 14 in accordance with the present invention. As shown, interior portion 12 has a number of items including interior panel trim 21, carpet 22, side panel and seat fabric 23, interior panel instruments 24, vent ducts 25, and steering wheel 26. Interior portion 12 of vehicle 10 may also include a headliner, a rear package tray, and fabric on rear seats (not shown). Exterior portion 14 has a number of items including exterior body 31, but may also include headlights, front and rear bumpers, and side mirrors (not shown). Moreover, vehicle 10 includes glass which includes front, rear and side windows 32.

Figure 2:
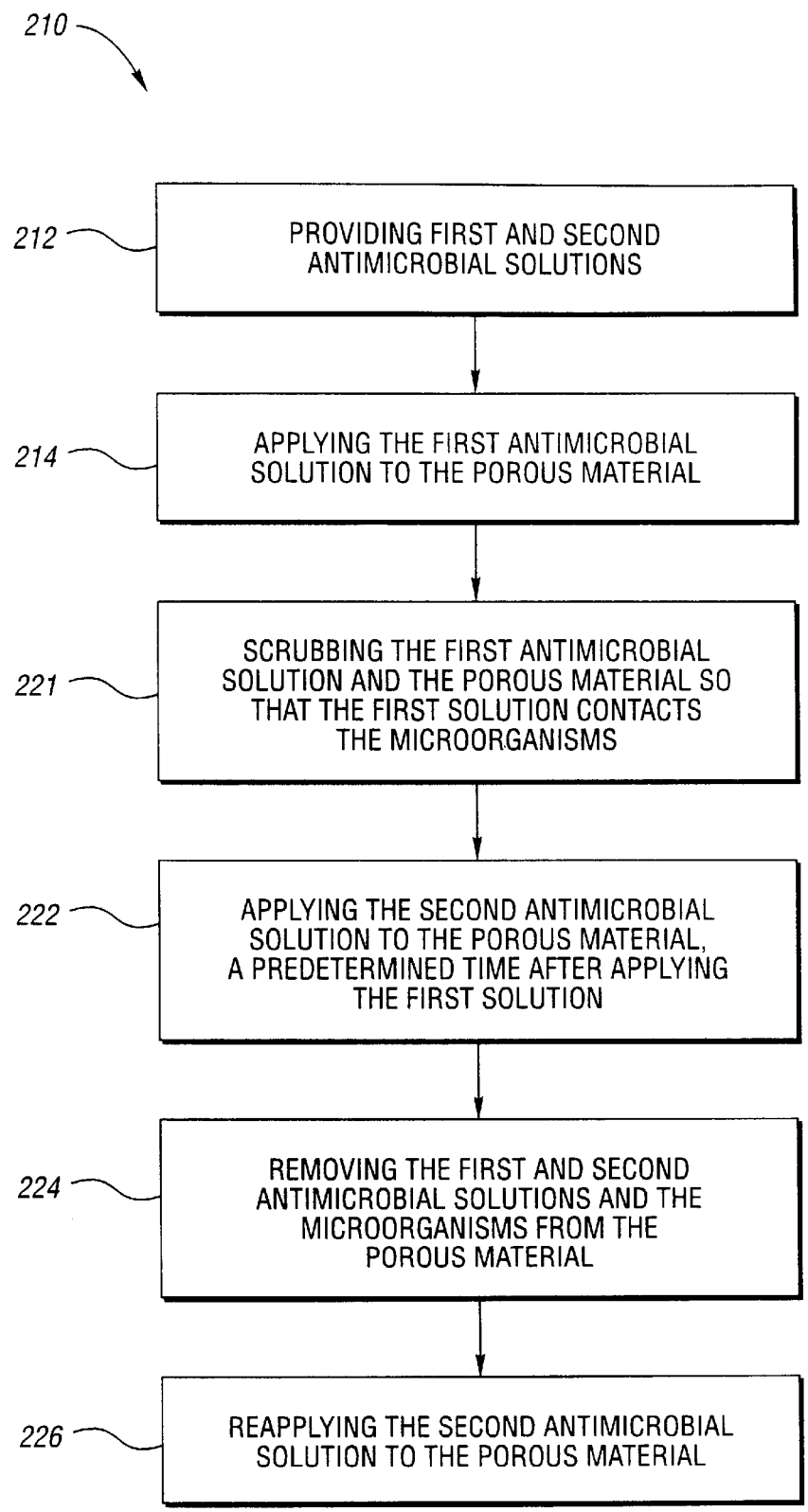
FIG. 2 is a flowchart of one embodiment of the present invention.

FIG. 2 depicts one embodiment of a method of treating a porous material of a vehicle in accordance with the present invention. The porous material may include cloth, fabric, carpet, or any other microorganism absorbing material disposed in or on vehicle 10. The porous material may be attached to any item of the vehicle to include side panel fabric, seat fabric, floor carpet, floor mat fabric, rear package tray fabric, headliner fabric or any other porous material on the vehicle capable of absorbing microorganisms. The porous material to be treated will typically have a measurable content of microorganisms thereon. The microorganisms mentioned herein include undesirable bacteria, viruses, or any other undesirable microorganisms. For example, such organisms may include but is not limited to *Spaphylococcus aureus, Escherichia coli, Listeria monocytogenes, Yersinia enterocolitica*, Salmonella, *Pseudomones ceruginosa*, Adenovirus Type 5, Herpes Simplex Type 1, Human Immune Deficiency Virus, Influenza $A_2$, Vaccinia, and Avian Influenza A. Thus, one embodiment of the present invention treats the porous material such that a substantial amount if not all of the microorganisms are removed from the porous material, e.g., about 99.9% removal.

As shown in FIG. 2, method 210 involves providing a first antimicrobial solution and a second antimicrobial solution in box 212. Preferably but not necessarily, the first and second solutions each include an n-Alkyl Dimethyl Benzyl Ammonium Chloride and n-Alkyl Dimethyl Ethylbenzyl Ammonium Chloride solution ("antimicrobial solution"). Preferably but not necessarily, the first solution includes about 0.025 weight percent of n-Alkyl Dimethyl Benzyl Ammonium Chloride and about 0.025 weight percent of n-Alkyl Dimethyl Ethylbenzyl Ammonium Chloride. Preferably but not necessarily, the second antimicrobial solution includes about 0.04 weight percent of n-Alkyl Dimethyl Benzyl Ammonium Chloride and at least about 0.04 weight percent of n-Alkyl Dimethyl Ethylbenzyl Ammonium Chloride. In this embodiment, in the first solution, the solvent is water and the antimicrobial solution is the product having the trade name BTC 2125 M Series™ manufactured by the Stepan Company of Northfield, Ill. Also in this embodiment, in the second antimicrobial solution the solvent is water and the antimicrobial solution is the product having the trade name BTC 2125 M Series™. Of course, any other suitable antimicrobial having n-Alkyl Dimethyl Benzyl Ammonium Chloride and n-Alkyl Dimethyl Ethylbenzyl Ammonium Chloride with the above-stated weight percents may be used.

Method 210 further includes applying the first antimicrobial solution to the porous material in box 214, such as to the floor carpet 22 or a floor mat carpet in the vehicle 10. This may be performed by using a spray gun or spray container having the first solution. Preferably but not necessarily, a spray device such as a poly-sprayer or Z-jet™ sprayer assembled by Ziebart International Corp. may be used. Of course, any other device capable of spraying the first solution onto the porous material may be implemented. Then, method 210 includes scrubbing the first antimicrobial solution and the porous material so that the first solution contacts the microorganisms to be removed in box 221. This may be completed by using an orbital mechanical scrubber (not shown). Of course, any other device having an automated movable brush may be used in the preferred embodiment. Additionally, scrubbing may be performed manually with a conventional brush. In this embodiment, the orbital scrubber is the product having the trade name Cycloscrubber™ manufactured by Cyclo Manufacturing Co. of Denver, Colo. On areas of the porous material which are not accessible to the orbital scrubber, the user may manually hand scrub the area so that the first solution contacts the microorganisms on the porous material.

Next, the method 210 includes applying the second antimicrobial solution heated to about 175° F. to the porous material, after a predetermined set time upon applying the first solution to the porous material in box 222. Preferably but not necessarily, the predetermined set time is approximately 10 minutes. It has been found that the best results in removing microorganisms from the porous material are obtained by waiting at least about 10 minutes. Of course, the user may wait a time greater than 10 minutes if desired. The method further includes immediately removing the first and second antimicrobial solutions and the microorganisms from the porous material in box 224. The steps of applying the second antimicrobial solution and removing the first and second antimicrobial solutions are preferably but not necessarily performed by using a hot water extractor wherein the second solution is first applied onto the porous material and then the antimicrobial solutions and the microorganisms are immediately removed therefrom. Any conventional hot water extractor may be used so long as the second solution may be applied before the solutions and microorganisms are removed. For example, the hot water extractor may be the product having the trade name DV-12 Therinator™, manufactured by Thermax of Reno, Nev. Furthermore, the method 210 includes reapplying the second solution to the porous material by spraying and wiping in box 226.

Figure 3:
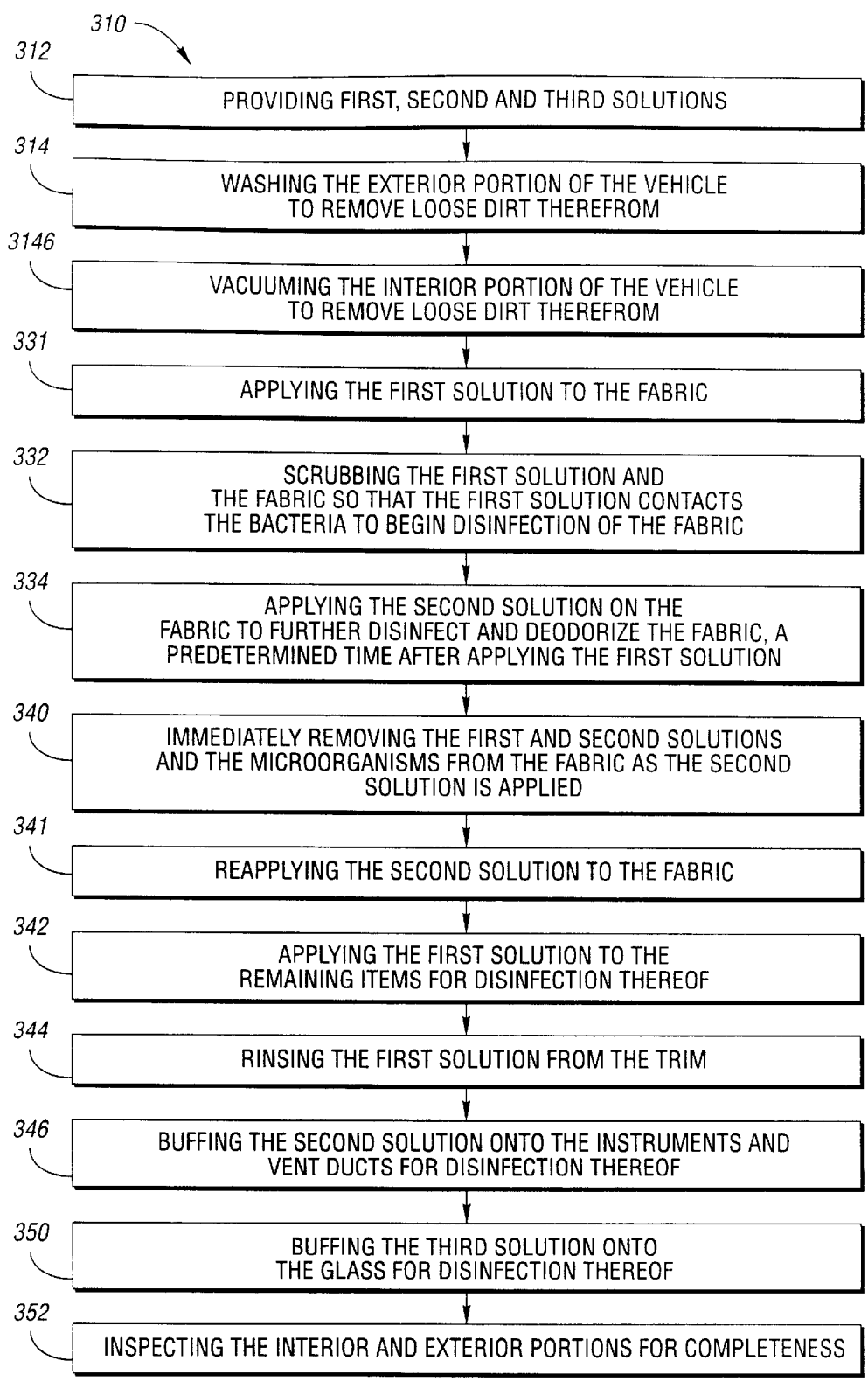
FIG. 3 is another embodiment of a method of treating a vehicle in accordance with the present invention.

FIG. 3 illustrates a flow chart of another embodiment in accordance with the present invention. Method 310 provides a method of treating a vehicle having interior and exterior portions and glass. Preferably, the vehicle is housed in a station wherein the following steps of method 310 are completed, such as a garage. Moreover, the following steps of method 310 may be completed by one or more users. In box 312, method 312 includes providing first, second, and third antimicrobial solutions. The first and second solutions may include n-Alkyl Dimethyl Benzyl Ammonium Chloride and n-Alkyl Dimethyl Ethylbenzyl Ammonium Chloride having the same weight percents as described above. The third solution is a glass cleaning solution which may be an Aromatic Halogen compound having a formula such as:

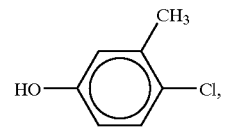

4-chloro-3-methylphenol.

For example, the third solution may be the product having the trade name Prevental CMK Preservative™ manufactured by Bayer Corp. Preferably, but not necessarily, the third solution includes about 0.05% of an aromatic hologen compound, e.g., 4-chloro-3-methylphenol. Of course, any other suitable antimicrobial glass cleaning products may be used. The exterior portion of the vehicle is then power washed to remove loose dirt therefrom as shown in box 314. Conventional power washers or hoses may be used to wash the exterior portion of the vehicle. In this embodiment, if the vehicle is going to receive any exterior paint service, then a first car wash concentrate is used. Preferably, the first car wash concentrate may be the product having the trade name Wash-N-Shine™ manufactured by Ziebart International Corp. Of course, any other suitable exterior cleaning solution may be used in accordance with the present invention. Then, the wheels and the tires of the vehicle are cleaned with a tire cleaning solution. For example, the tire solution may be the product having the trade name Shop Cleaner Plus™ manufactured by Ziebart International Corp. Of course, any other suitable tire cleaning solution may be used. Then, the exterior portion of the vehicle is rinsed with water and dried with dry cloths and/or chamois. Finally, the tires are dressed with a tire and rubber dressing.

Then, method 310 includes treating of the interior portion of the vehicle. First, all loose items in the interior compartments of the vehicle are removed therefrom. Moreover, removable floor mats are removed from the floor of the interior compartments. Additionally, the user inspects for ashtrays. If ashtrays need cleaning, the ashtrays are removed, emptied, and cleaned with a cleaning solution, preferably with the first solution. Of course, any other suitable antimicrobial solution may be used. Next, as shown in box 316, the interior seats, carpets, floor mats, and other items having porous material thereon are vacuumed thoroughly. The user then inspects the interior portion for spots and stains. If spots and stains are found, then the user applies stain removal solution thereto. Any suitable stain removal solution may be used.

As shown in box 331, method 310 further includes applying the first solution to the upholstery, carpet, floor mats, seat belts and other interior items having porous material thereon. This may be accomplished by using a spray device mentioned above. The user then allows the first solution to set for approximately ten minutes. During this time period, Applicants believe that the porous materials, e.g. the upholstery, carpet, floor mats, seat belts and other interior items, experience sanitizing, disinfecting, virucidal activities which reduce, if not eliminate, the level of microorganisms on the porous material. Then, as in box 332, the user scrubs the upholstery, carpet, floor mats, etc. using an orbital scrubber as mentioned in the embodiment above. Areas that are not accessible to the scrubber may be hand scrubbed by the user with any brush. As shown in box 334, the user then applies the second solution heated at about 175° F. on the interior items, e.g. upholstery, carpet, floor mats, and seat belts, to further disinfect, sanitize, virucide, and deodorize the fabric, after a predetermined time e.g., ten minutes, of applying the first solution. Then, the first and second solutions and the microorganisms are immediately removed from the areas as the second solution is applied as shown in box 340. This may be completed with a hot water extractor containing the second solution heated at about 175° F. Then, the second solution is reapplied onto the interior items by spraying and wiping in box 341.

Moreover, in box 342, remaining items in the interior portion of the vehicle, e.g., vinyl and plastic interior trim, is cleaned with a cloth saturated with the first solution. Then, in box 344, a dry clean cloth or a damped cloth with water may be used to rinse and dry the remaining items. Additionally, a light coat of vinyl dress solution may be applied to the vinyl and plastic trim with a clean cloth. As shown in box 346, portions of the interior panel, such as vent ducts and panel instruments, are cleaned with a clean cloth damped with the second solution. The tire and rubber dressing as described may be used to clean and dress door seals. Remaining items not mentioned above may also be cleaned as desired. For example, if a dome light appears to need cleaning, then the user may clean the dome light with the first solution. Moreover, the headliner, rear package tray, and cargo area carpeting/mat may also be cleaned with the second solution, if needed. In many situations, cleaning of these items is a manual activity, since the scrubbing device would not typically be able to reach these areas.

If the interior portion of the vehicle has leather seats, the leather seats are cleaned by using a soft clean cloth moistened with the first solution. The leather is then dried with another clean cloth. Then, a leather conditioner is applied to the leather seats and is allowed to set for about five minutes. After about five minutes, the leather seats are buffed with a clean dry cloth to remove the excess leather conditioner. The leather conditioner may be any suitable leather conditioning solution.

Next, the third solution is applied to glass items by spraying and wiping on a windshield, side windows and a rear window of the vehicle. The applied third solution is sprayed onto the glass and wiped with a dry cloth, as shown in box 350.

After cleaning, all removed items are returned back to the interior portion of the vehicle, including floor mats, ashtrays, and all other loose items which were removed prior to treatment of the interior portion of the vehicle. Furthermore, as shown in box 352 method 310 includes completing a quality card which may be a checklist for the user to assure all steps of the process are completed. Optionally, a final inspection may be made by the user or another user. Finally, paper floor mats are installed in the interior portion of the vehicle along with a plastic seat cover for each seat.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of treating a vehicle, the vehicle having interior and exterior portions and glass, the interior portion including a trim, a fabric, instruments, and a vent duct having bacteria, the method comprising:

providing first, second and third antimicrobial solutions;

washing the exterior portion of the vehicle to remove loose dirt therefrom;

vacuuming the interior portion of the vehicle to remove loose dirt therefrom;

applying the first antimicrobial solution to the fabric;

scrubbing the first antimicrobial solution and the fabric so that the first solution contacts the bacteria to begin disinfection of the fabric;

applying the second antimicrobial solution at a predetermined temperature on the fabric to further disinfect and deodorize the fabric, after applying the first solution a predetermined time;

immediately removing the first and second solutions and the bacteria from the fabric as the second solution is applied;

reapplying the second solution to the fabric;

applying the first solution to the trim for disinfection thereof;

rinsing the first solution from the trim;

applying the second solution onto the instruments and vent ducts for disinfection thereof;

applying the third solution onto the glass for disinfection thereof; and inspecting the interior and exterior portions for completeness.

2. The method of claim 1 further comprising:

cleaning wheels and tires of the vehicle using a tire cleaning solution; and dressing the tires with a tire and rubber dressing.

3. The method of claim 1 wherein washing the exterior portion of the vehicle includes:

using a wash concentrate solution, if the vehicle is to receive an exterior paint service; and using a wash shine solution, if the vehicle will not receive an exterior paint service.

4. The method of claim 1 further comprising drying the exterior portion of the vehicle with chamois.

5. The method of claim 1 further comprising:

removing all loose items in the vehicle, before vacuuming the interior portion of the vehicle; and returning the loose items to vehicle, after vacuuming.

6. The method of claim 1 herein the interior portion further includes seats, carpet, floor mats, and a cargo area.

7. The method of claim 6 further comprising:

applying a leather conditioner to the seats, if the seats are leather;

buffing the leather conditioner onto the seats; and drying the seats.

8. The method of claim 1 further comprising:

inspecting the interior portion of the vehicle for spots an stains; and removing spots or stains, if spots or stains are found in the interior portion of the vehicle.

9. The method of claim 1 further comprising:

applying a light coat of a vinyl clean dress solution to the trim, after rinsing the first solution from the trim; and buffing the vinyl clean dress solution onto the trim.

10. The method of claim 1 further comprising cleaning door seals of the vehicle with a tire and rubber dressing solution.

11. The method of claim 1 further comprising cleaning the dome light of the vehicle with the first solution.

12. The method of claim 1 further comprising spraying the second solution onto the headliner, rear package tray, trunk carpeting of the vehicle.

13. The method of claim 1 wherein the first a antimicrobial solution includes an n-Alkyl Dimethyl Benzyl Ammonium Chloride and n-Alkyl Dimethyl Ethylbenzyl Ammonium Chloride solution.

14. The method of claim 13 wherein the first a antimicrobial solution includes about 0.025 weight percent of n-Alkyl Dimethyl Benzyl Ammonium Chloride and about 0.025 weight percent of n-Alkyl Dimethyl Ethylbenzyl Ammonium Chloride.

15. The method of claim 1 wherein the second antimicrobial solution includes an n-Alkyl Dimethyl Benzyl Ammonium Chloride an n-Alkyl Dimethyl Ethylbenzyl Ammonium Chloride solution.

16. The method of claim 15 wherein the second antimicrobial solution includes about 0.04 weight percent of n-Alkyl Dimethyl Benzyl ammonium Chloride and about 0.04 weight percent of n-Alkyl Dimethyl Ethylbenzyl Ammonium Chloride.

* * * * *

UNITED STATES PATENT AND TRADEMARK OFFICE
CERTIFICATE OF CORRECTION

PATENT NO.   : 6,682,606 B2
DATED        : January 27, 2004
INVENTOR(S)  : Thomas R. Walker It is certified that error appears in the above-identified patent and that said Letters Patent is hereby corrected as shown below:

Column 6,
Line 63, delete "herein" and insert -- wherein --

Column 7,
Line 4, delete "an"and insert -- and --

Column 8,
Lines 1 and 5, delete "a"

Signed and Sealed this

Twenty-fifth Day of January, 2005

JON W. DUDAS
*Director of the United States Patent and Trademark Office*